United States Patent
Rust et al.

(10) Patent No.: US 6,448,030 B1
(45) Date of Patent: Sep. 10, 2002

(54) METHOD FOR PREDICTING THE EFFICACY OF ANTI-CANCER DRUGS

(75) Inventors: William L. Rust, Las Vegas; Janice L. Huff; George E. Plopper, both of Henderson, all of NV (US)

(73) Assignee: University of Nevada-Las Vegas ( * ) Notice: Subject to any disclaimer, the term of this patent is extended or adjusted under 35 U.S.C. 154(b) by 54 days.

(21) Appl. No.: 09/730,700

(22) Filed: Dec. 5, 2000

Related U.S. Application Data (60) Provisional application No. 60/183,628, filed on Feb. 18, 2000.

(51) Int. Cl.[7] ............................. C12Q 1/02; C12Q 1/00; G01N 33/53

(52) U.S. Cl. ............................. 435/29; 435/4; 435/968; 422/186

(58) Field of Search ............................. 435/29, 4, 968; 422/186

(56) References Cited

U.S. PATENT DOCUMENTS

| | | | |
|---|---|---|---|
| 4,816,395 A | | 3/1989 | Hancock et al. |
| 4,937,182 A | | 6/1990 | Hancock et al. |
| 5,145,863 A | * | 9/1992 | Doughtery ............... 514/410 |
| 5,601,997 A | * | 2/1997 | Tchao ........................ 435/29 |
| 5,801,055 A | | 9/1998 | Henderson |

OTHER PUBLICATIONS

Current Status and Future Directions of Chemosensitivity Testing, Bernd–Uwe Sevin et al., Contrib Gynecol Obstet. Basel, 1994, vol. 19, pp 179–194.

Prediction of Response to Drug Therapy of Cancer, A Review of In Vitro Assays, William T. Bellamy, pp. 680–708.

Chemosensitivity Testing: A Critical Review, Critical Reviews in Clinical Labortory Sciences, Andrew B. Cramer et al., vol. 28 Issue 5,6 (1991).

In Vitro Assays for chemotherapy sensitivity, Robert M. Hoffman, Critical Reviews in Oncology/Hematology 15 (1993) 99–111.

Improvement of In Vitro Chemosensitivity Assay for Human Solid Tumors by Application of a Preculture Using Collagen Matrix, Akihiro Kitaoka et al., Clinical Cancer Research, vol. 3 295–299 Feb. 1997.

Anticancer Chemosensitivity and Growth Rate of Freshly Separated Human Colorectal Cancer Cells Assessed by in Vitro DNA Synthesis Inhibition Assay, Kazuya Kawabata et al., Anticancer Research 18: 1633–1640 (1998).

(List continued on next page.)

*Primary Examiner*—Louise N. Leary
(74) *Attorney, Agent, or Firm*—Quirk & Tratos (57) ABSTRACT

A method for measuring both the anti-migratory and cytotoxic effects of anticancer drugs on cancer tissues measuring the chemosensitivity of human biopsies to therapeutic drugs. Single cell suspension preparations of biopsy tissue is exposed to anticancer drugs and introduced into the first chamber of a migration plate separated from a second chamber by a porous membrane opaque to radiation. A migration stimulus is added to the second chamber. Migrated cells on the side of the membrane facing the second chamber are labeled with a live-cell fluorescent indicator. Non-migrated cells on the side of the membrane facing the first chamber are labeled with a fluorescent indicator of cell death. The emitted fluorescence of both the migrated cells and the non-viable cells is quantified in a fluorescence plate reader. The comparative intensity of fluorescence is an indicator of the susceptibility of the cells to the cytotoxic properties of the drug.

9 Claims, 4 Drawing Sheets

OTHER PUBLICATIONS

Clinical Applications of the Histoculture Drug Response Assay, Toshiharu Furakawa et al., Clinical Cancer Research vol. 1, 305–3011, Mar. 1995.

The Usefulness of the ATP Assay with Serum–free Culture for Chemosensitivity Testing of Gastriontestinal Cancer, H. Kawamura et al., Eur J Cancer, vol. 33, No. 6, pp. 960–966, 1997.

Screening Assay Promigratory/Amtimigratory Compounds, Will L. Rust et al., Analytical Biochemistry 280, 11–19 (2000).

A Novel Cytotoxicity Screening Assay Using a Mulitwell Fluorescence Scanner, Anna–Liisa Nieminen et al., Toxicol. Appl. Pharmacol. 115, 147–155.

* cited by examiner

METHOD FOR PREDICTING THE EFFICACY OF ANTI-CANCER DRUGS

REFERENCE TO RELATED APPLICATION

This application is a continuation of co-pending provisional patent application Ser. No. 60/183,628 filed Feb. 18, 2000, entitled Method and System for in Vitro Screening of Compounds for Pro/Anti-Migratory Effects.

BACKGROUND OF THE INVENTION

1. Field of the Invention

The present invention relates to assays for predicting the chemosensitivity of tissues to particular drugs, and more specifically to a method for measuring both the anti-migratory effect and cytotoxic effect of drugs on tissues in vitro.

2. Description of Prior Art

Solid tissue cancers are broadly defined by two general characteristics, namely: (1) a mass of hyperproliferating cells of clonal origin, and (2) acquisition of an aggressively invasive phenotype, wherein cancer cells leave the tissue of origin and establish new tumor metastases at distant sites. Current methods for evaluating the effect of accepted and experimental anti-cancer drugs on human cancers focus on measuring the arrest of hyperproliferation or the stimulation of cell death, both markers of only the first characteristic of cancer.

In general, these current methods require that single cells be isolated from a tumor biopsy and then grown in a culture. The cultured cells are then exposed to a drug, and after a certain amount of time has elapsed cytostatic or cytotoxic effects are measured. These measurements are made in many ways, including: incorporation of the toxic substance, inducement of programmed cell death (termed apoptosis), depletion of intracellular metabolites such as adenosine triphosphate (ATP), depression of cell growth, and compromise of the cell membrane.

The most significant drawback of these methods is the inability to assess the effect of anticancer drugs on the second, and most lethal, characteristic of cancers, i.e., the invasive characteristic that leads to establishment of tumors at distant sites. Other drawbacks include:

1. The requirement to grow/expand biopsy cells in culture before testing allows selective expansion of subsets of tumor cells that are not necessarily representative of the entire tumor. In addition, many biopsies suffer from low plating efficiency, precluding them from being tested.
2. Measurements of cellular metabolism cannot discriminate cells that are injured and will recover from those which are truly dead.
3. Assays using differential staining techniques are subject to individual interpretation, and frequently cannot distinguish live cells from cellular debris.
4. All assays that measure a single biochemical endpoint, such as cell proliferation or inhibition of DNA synthesis are limited by the particular characteristics of that endpoint, and do not accurately reflect cell survival.
5. These assays suffer from long turn-around time, ranging from 5 days to several weeks.

It is therefore desirable to provide an alternative assay for measuring the chemosensitivity of cancer biopsies that does not require the expansion of cells in culture, can assess the effect of anticancer drugs on both the hyperproliferation and invasive characteristics of human cancers, that is not dependent on cell metabolism or differential staining, and can be performed quickly with a minimum of manipulations.

Alternative assays proposed to predict the chemosensitivity of biopsies in vitro can be found in U.S. Pat. Nos. 4,816,395 and 4,937,182. A review of several chemosensitivity assays that use metabolite production and hyperproliferation analysis as chemosensitivity determinants is given by Bellamy, W. T., Prediction of response to drug therapy of cancer. A review of in vitro assays. Drugs 44(5): pp 690–708, (1992), Sevin, B. U., et al., Current status and future directions of chemosensitivity testing. Contrib Gynecol Obstet 19: pp 179–194, (1994), and Cramer, A. B., et al., Chemosensitivity testing: a critical review. Crit Rev Clin Lab Sci 28(5–6): pp 405–413 (1991, Hoffman, R. M., In vitro assays for chemotherapy sensitivity. Crit Rev Oncol Hematol 15(2): pp 99–111, (1993). A chemosensitivity assay using radioactive nucleotide incorporation is given by Kitaoka A., et al, Improvement of in vitro chemosensitivity assay for human solid tumors by application of a preculture using collagen matrix. Clin Cancer Res 3(2): pp 295–299, (1997). A method using DNA synthesis as an indicator of cell growth is given by Kawabata, K. et al., Anticancer chemosensitivity and growth rate of freshly separated human colorectal cancer cells assessed by in vitro DNA synthesis inhibition assay. Anticancer Res 18(3A): pp 1633–1640 (1998). Chemosensitivity assays that measure cell viability by cellular metabolism are: Furukawa, T., et al., Clinical applications of the histoculture drug response assay. Clin Cancer Res 1(3): pp 305–311, (1995), and Kawamura, H., et al., The usefulness of the ATP assay with serum-free culture for chemosensitivity testing of gastrointestinal cancer. Eur J Cancer 33(6): pp 960–966, (1997). An embodiment of the present invention is described in Rust, W. L., Screening assay for promigratory/antimigratory compounds. Anal Biochem 280(1) pp 11–19, (2000). Each of these suffers from at least one of the disadvantages listed above.

The present invention takes advantage of several aspects of a procedure for automatically measuring cell migration described in U.S. Pat. No. 5,601,997 to Tchao, modified and adapted for the novel use described herein. The present invention further incorporates for novel use the cell death determination procedure described by Nieminen, A. L., A novel cytotoxicity screening assay using a multiwell fluorescence scanner. Toxicol Appl Pharmacol 115(2): pp 147–155, (1992).

BRIEF SUMMARY OF THE INVENTION

The present invention provides the first efficient method for simultaneously measuring the anti-migratory effect and cytotoxic effect of drugs on biopsy cells without the need to expand the cells in culture. This assay is particularly useful for predicting the chemosensitivity of an individual patient's cancer to therapeutic drugs. This assay is unique among chemosensitivity assays for the ability to measure both the anti-migratory and cytotoxic effects of drugs. Because the formation of solid tissue cancer is dependent upon the invading cell's ability to migrate across tissues as well as hyperproliferation, a chemosensitivity assay that measures the both the anti-migratory and cytotoxic effect of drugs is a more comprehensive and more sensitive method for determining the chemosensitivity of biopsies than other assays. Moreover, obviating the need to expand cells in culture reduces the risk of experimental factors which can bias the assay outcome, and allows the assay to be performed more quickly than current methods.

In accordance with the present invention biopsy samples are dissociated into individual cells which are exposed to anticancer drugs and introduced into a top chamber of a migration assay apparatus. A stimulant then induces the cells to migrate across a porous membrane. After a period of time, migrated cells are labeled with a live cell fluorescent indicator and non-migrated cells are labeled with a fluorescent indicator of cell death. The fluorescence of both fluorophores are measured in a fluorescence plate reader. The fluorescence intensity of the cell death reporter indicates the sensitivity of the cells to cytotoxic effects of the drugs. The fluorescence emitted from the migrated cells indicates ability of the biopsy cells to migrate in the presence of the drugs.

Significantly, the present invention is distinct from all the prior art, including the procedure described in U.S. Pat. No. 5,601,997 to Tchao, in that the prior art procedures all require that the cells in the assay be first pre-labeled. The presence of a labeling chemical dye in the prior art procedures can influence migration behavior and may interact with the chemical agent being tested. In contradistinction, the inventive assay does not introduce chemical agents into the process, as it is not intended to for kinetic analysis of the migratory behavior of cells, and the incorporation of a cytotoxic assay into the procedure is entirely novel.

DETAILED DESCRIPTION OF THE INVENTION

The present invention is an assay for simultaneously and automatically measuring the antimigratory and cytotoxic properties of anticancer drugs on human tissues. This assay is useful for predicting the chemosensitivity of biopsy samples to various chemical agents or combinations of chemical agents. A flow chart describing the steps of the present invention is provided in FIG. 1 carried out in its substantial aspects in a migration plate structure illustrated in FIG. 2, which in its detailed form may be like that described in U.S. Pat. No. 5,801,055. In step 101 of FIG. 1 the cells of a biopsy are disaggregated by gentle mechanical agitation and/or proteolytic digestion in a serum free medium suitable for maintaining the cells in culture. In steps 102 and 103 the cells are exposed to an anticancer chemical agent and introduced into the first chamber 8 of a migration plate. The anticancer drug is directly added to the cell suspension to reach a final concentration typically in the range of 1 to 100 µMolar. The top chamber 8 of the migration plate is separated from a second chamber 10 by an electromagnetic radiation opaque membrane having a plurality of substantially perpendicular transverse pores 9. A migration stimulus is then added to the second chamber 10 which may be a chemotactic stimulus, (a chemical dissolved in the medium of the second chamber), or a haptotactic stimulus, (a non-solubilized molecule adhered to the radiation opaque membrane on the side facing the second chamber). In step 104 the cells are then allowed to migrate in the appropriate conditions (temperature, pH, humidity, and carbon dioxide concentration) from the first chamber through the pores of the radiation opaque membrane towards the second chamber in conditions suitable to maintain human tissues, e.g., 37° C., pH 7.4, 5% carbon dioxide.

Figure 1:
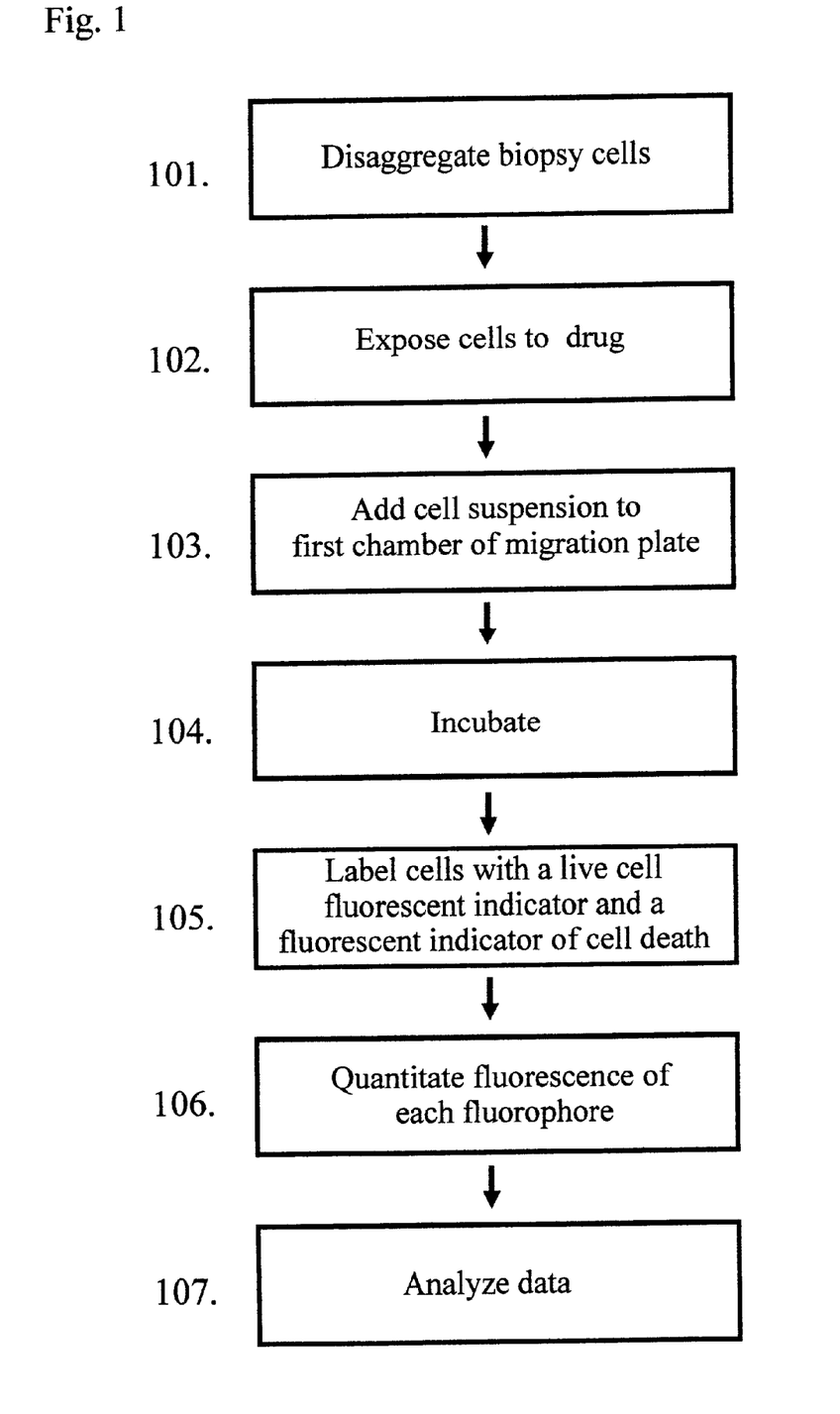
FIG. 1 is a flow chart illustrating each step of the present invention for predicting the efficacy of anti-cancer drugs on human tissue.
Figure 2:
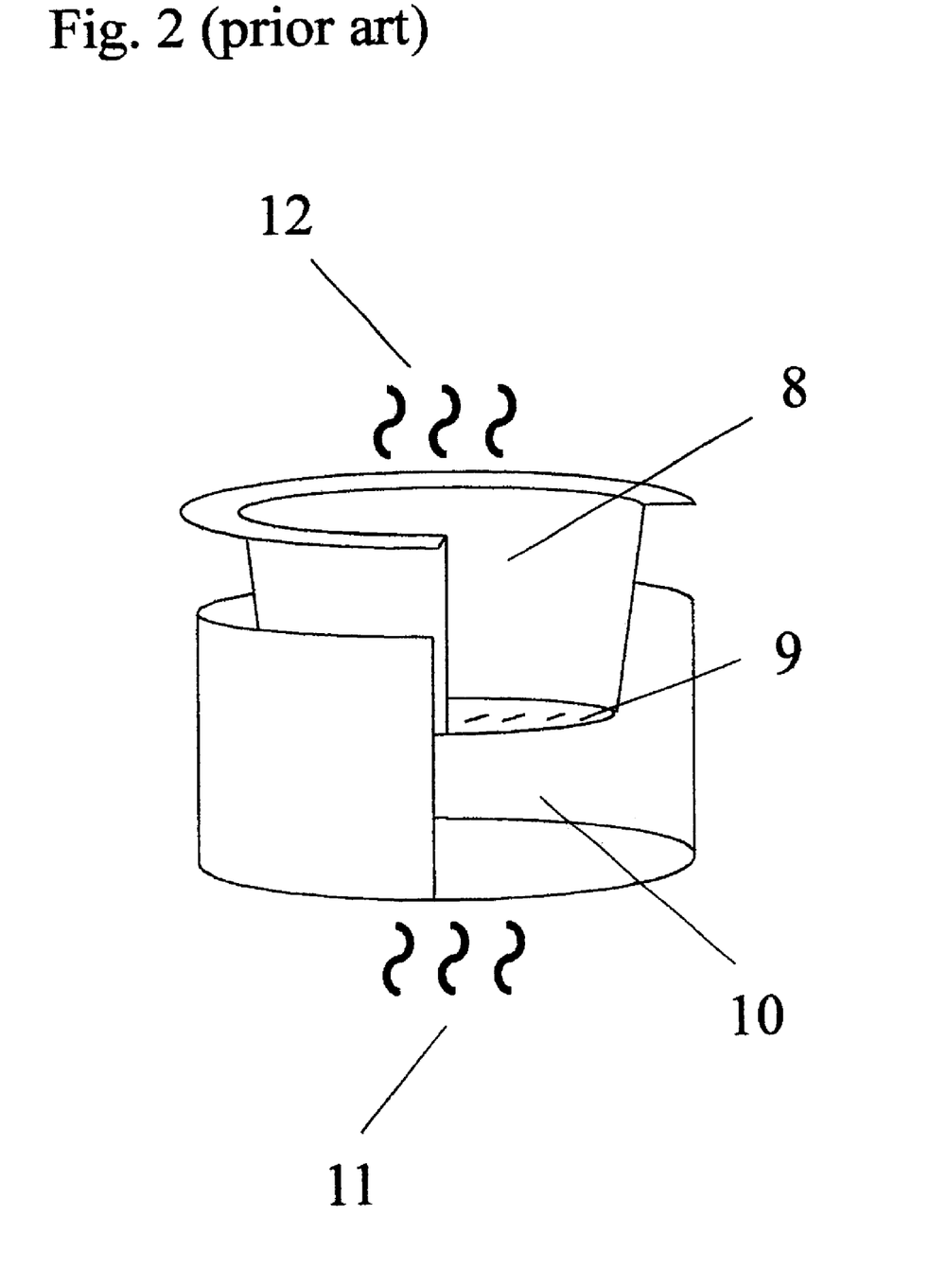
FIG. 2 is an illustrative diagram of the test chambers of a suitable migration plate apparatus useful with the present invention.

After a predetermined amount of time, typically 4–24 hours, the cells adhered to the side of the membrane facing the second chamber are labeled with a live-cell fluorescent indicator in step 105. The non migrated cells which remain adhered to the side of the membrane facing the first chamber are labeled with a fluorescent indicator of cell death. In each instance the fluorophores are added directly to the medium to reach a final concentration typically from 1–50 micro Molar. Live cell fluorescent indicator suitable for quantitating migrated cells include metabolic dyes such as calcein-AM, membrane dyes such as DiO, DiI, or fluorescent microspheres that are spontaneously endocytosed by live cells. Fluorescent indicators suitable for quantifying cell death include ethidium bromide and propidium iodide. The mechanism of action of these indicators is the enhancement of fluorescence intensity upon binding deoxyribonucleic acid (DNA). These dyes easily permeate the compromised membranes of dead cells but are largely excluded from live cells. The fluorophores must be chosen such that the migration plate membrane is opaque to either the excitation or emission or both wavelengths of the fluorophore. In step 106 the intensity of the electromagnetic radiation emitted from the fluorophores on either side of the membrane are measured in a fluorescence plate reader. An example of a suitable fluorescence plate reader is the SpectraFluor manufactured by TECAN (Research Triangle Park, NC). Then in step 107, the last step of the invention the analysis of the emitted fluorescence data is carried out. The fluorescence II emitted from the live cell fluorescent indicator on the side of the membrane facing the second chamber is an indicator of the amount of cells that have migrated across the filter. The fluorescence 12 emitted from the fluorescent indicator of cell death on the side of the membrane facing the first chamber is an indicator of the amount of cells that are not viable. The strength of these signals indicate the chemosensitivity of the cells to the drug being tested. A strong relative emission from the first chamber indicates sensitivity to cell death induced by the chemical. A weak relative emission from the second chamber indicates sensitivity to inhibition of migration induced by the chemical. The data offer meaningful predictions of chemosensitivity of the cancer cells when compared to appropriate drug-free controls and to other drugs.

A potential limitation of the method described is the contamination of biopsy samples by non-tumorigenic cells that could potentially influence assay results. Epithelial cultures, in particular, are prone to fibroblast contamination and this cell type predominates the colon, breast, and lung cancer biopsies. The extent of fibroblast contamination can be determined by double immunofluorescence staining using antibodies specific for the intermediate filament protein subunits vimentin (as a marker for fibroblasts) and keratin (for epithelial cells).

The methods of the present invention are useful with a wide variety of cells. These include solid tumor cells of biopsies derived from breast, colorectal, lung, and other tissues, and hematopoietic cells. The tumor cells may be of epithelial origin (carcinomas), arise in the connective tissue (sarcomas), or arise from specialized cells such as melanocytes (melanomas) and lymphoid cells (lymphomas), and the like. The cells may be derived from primary tumors or metastatic tumors.

The anti-cancer drugs which may be assessed by the assay of present invention include natural or synthetic, common or experimental drugs. Compounds which are only effective after being metabolised by the body must be used in their active conformation.

EXAMPLES

The following examples are offered by way of illustration, not by way of limitation.

Cell Sample Preparation

Upon biopsy and/or surgical removal, tumor samples were aseptically transferred to tubes containing RPMI 1640 cell culture media (Irvine Scientific, Santa Ana, Calif.) supplemented with penicillin (100 U/ml) and streptomycin (100 $\mu$g/ml). Sample size was approximately 1 cm in diameter. Tissues were minced with a sterile razor into pieces less than 1 mm$^3$. Single cells were separated from tissue fragments by filtration through two sheets of sterile gauze (16XX mesh). Cells were collected by centrifugation and washed with phosphate buffered saline, repelleted and resuspended in migration media preferrably comprising of Dulbecco's modified eagle's medium (DME, Irvine Scientific, Santa Ana, Calif.) supplemented with 1 mM sodium pyruvate and 292 $\mu$g/ml L-glutamine, 100 U/ml penicillin, and 100 $\mu$g/ml streptomycin. For proteolytic digestion, tissues were first minced into approximately 3 mm$^3$ pieces and added to media containing collagenase and dispase and incubated for approximately 30 minutes at 37° C. with gentle agitation. The cells were then allowed a rest period ranging from 1 to 12 hours in a humidified incubator maintained at 37° C. and 5% carbon dioxide.

Introduction Into Assay Apparatus

The cell suspension was added to the first chamber of a migration plate containing 96 chambers per plate at a concentration of about 80,000 cells per chamber. The migration plate used in this assay was manufactured by Polyfiltronics. Similar plates are available from Becton-Dickinson (U.S. Pat No. 5,801,055). The second chamber contained either haptotactic stimulus in the form of 20 $\mu$g/ml fibronectin or chemotactic in the form of 5% fetal calf serum. Cells were allowed to migrate in a humidified incubator at 37° C. and 5% carbon dioxide for twelve hours.

Labeling Cells With Fluorescent Indicator

During the last half hour of the incubation, calcein-AM (Molecular Probes, Eugene, Oreg.) was added to the second chamber to a final concentration of 5 $\mu$M and propidium iodide was added to the first chamber to a final concentration of 30 $\mu$M. At the end of the incubation the underside of the filters were washed twice in phosphate buffered saline. Fluorescence from each individual well chamber was measured from the bottom using 485 nm excitation and 530 nm emission filters.

The Assay

Figure 3A:
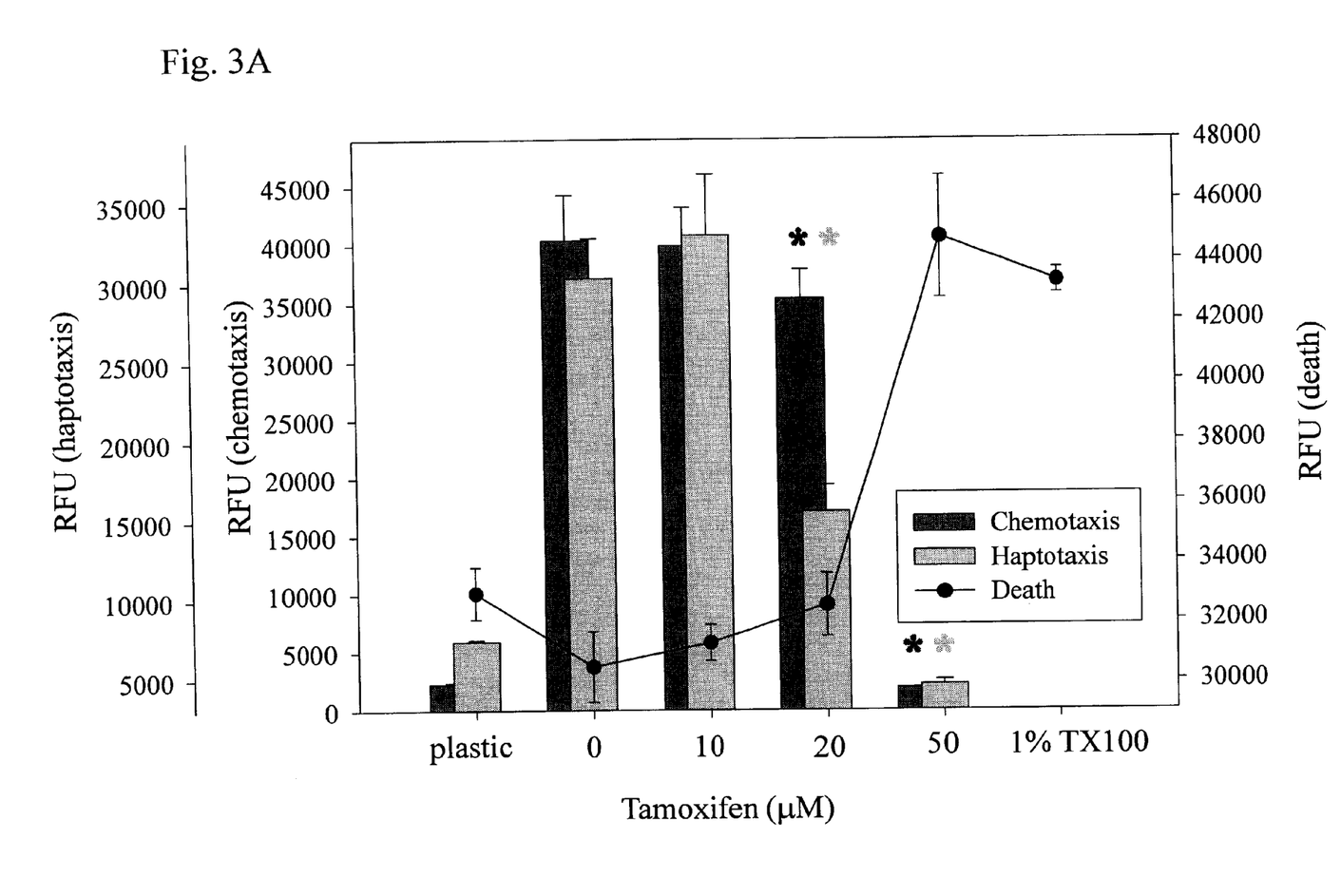
FIGS. 3A and 3B are exemplary comparison charts of the sensitivity of human breast cancer cells to the anti-migratory and cytotoxic effects of two anticancer drugs wherein the anticancer drugs compared are the common anticancer drug tamoxifen (FIG. 3A) and an experimental anticancer drug carboxyamido-triazole (FIG. 3B). Breast cancer cells were allowed to migrate towards serum (chemotaxis) or fibronectin (haptotaxis) in the presence of tamoxifen (a) and carboxyamido-triazole (CAI) (B). After 18 hours, migrated cells were labeled with calcein-AM and fluorescence quantitated from the bottom. Nonmigrated cells were labeled with propidium iodide and fluorescence quantitated from the top. Estimation of 100% cell death was made by lysing cells in a test chamber with 1% Triton X-100 (TX 100) Error bars represent the standard deviation of 4–16 replicate test chambers. Asterisks represent a significant difference from migration without drugs (P<0.05). RFU=relative fluorescence units.
Figure 3B:
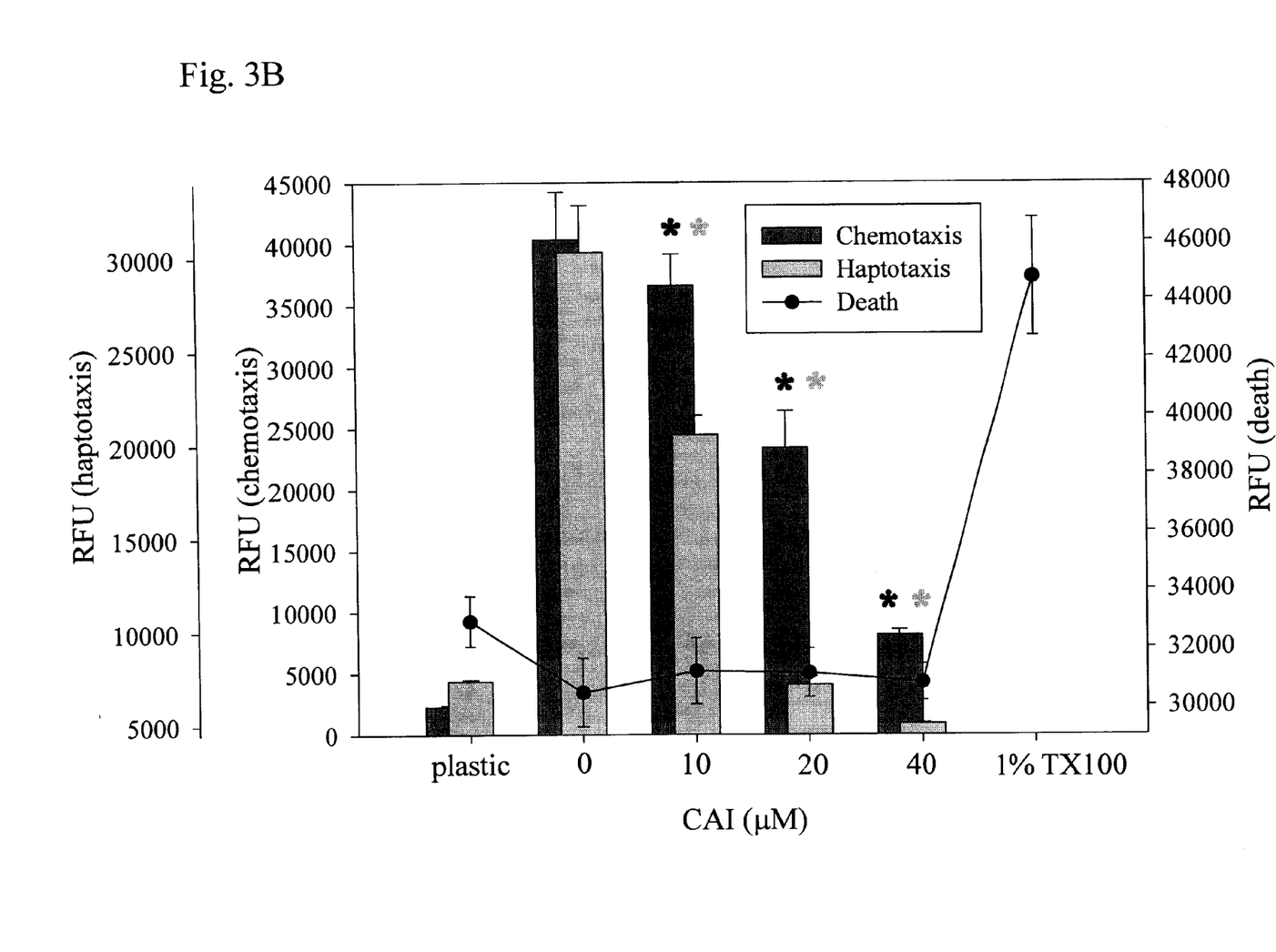

Fluorescence from each individual well chamber was measured from the top using 560 nm excitation and 645 nm emission wavelength filters using a Tecan SpectraFluor fluorescent plate reader (Research Triangle Park NC). FIG. 3 demonstrates the influence of tamoxifen and carboxyamido triazole (CAI) on the migration and viability of highly metastatic breast cells. The dynamics of inhibition of migration are different than cytotoxic effects caused by drug exposure (FIGS. 3A, 3B). Both haptotactic and chemotactic migration are inhibited at lower concentrations than those that cause cell death for both tamoxifen and CAI (FIGS. 3A, 3B). Tamoxifen and CAI inhibited migration in a dose-dependent manner at sublethal concentration, and CAI was more effective than tamoxifen at halting migration. Haptotactic migration on fibronectin was more sensitive to drug effects than chemotactic migration. Cells exposed to 10 $\mu$M CAI demonstrated 32% inhibition of haptotaxis and 7% inhibition of chemotaxis. At 20 $\mu$M, CAI abolished haptotaxis and inhibited chemotaxis by 42% (FIG. 3B). Cells exposed to tamoxifen demonstrated non-significant inhibition of chemotaxis and haptotaxis at 10 $\mu$M, and only 51% inhibition of haptotaxis and 9% inhibition of chemotaxis at 20 $\mu$M (FIG. 3A). These cells were more sensitive to the cytotoxic effects of tamoxifen than CAI as evidenced by the increased propidium iodide fluorescence (FIG. 3A, 3B). The asterisks represent a significant difference from positive control ($p<0.05$).

Alternative Embodiments

With the following modifications, the present invention is useful as a tool for discovery of novel anticancer compounds and cancer preventative compounds. A cancer preventative compound is described here as a drug that substantially inhibits the migration of cancer cells but does not inhibit cell proliferation. Such a drug would potentially not cause to the patient the side effects typical of anti-proliferative compounds. These side effects include damage to normal tissues, immune suppression, mucositis, hair loss, nausea, and vomiting.

In this embodiment, established cultured cell lines are used in place of biopsy samples. These cell lines serve as representative examples of human cancers from a range of tissues such as breast, lung, bone, colon, prostate, etc. Experimental compounds are added to suspensions of cultured cells to reach a final concentration typically in the range of 1–100 $\mu$M. These compounds are typically stored in dimethyl sulfoxide, a chemical toxic to cells. For that reason, care must be taken to limit the dimethyl sulfoxide concentration to an amount not harmful to the cells, typically <50 $\mu$M. The chemosensitivity assay is performed as described in the main embodiment. Promising anticancer compounds are defined as those which substantially inhibit migration and induce cell death in a cancer cell type. Promising cancer preventative compounds are defined as those that inhibit cell migration without inducing cell death.

Conclusion, Ramifications, and Scope

The present invention of a method for quantifying the chemosensitivity of cancer cells to anticancer compounds has the following advantages over other chemosensitivity assays. The present invention measures an endpoint characteristic of metastasis formation, a feature unique among chemosensitivity assays. The present invention measures two endpoints of anticancer effect instead of just one, making the assay more comprehensive, and not specific to one cell response. The present invention does not require that biopsy cells be expanded in culture, thus shortening the time frame of the assay and avoiding the bias that culturing causes by selecting a subset of biopsy cells. Also, the present invention has the advantage over most other chemosensitivity assays in that results are quantified automatically, thus avoiding the bias inherent in subjective sampling by humans.

While my above description contains many specifics, these should not be construed as limitations on the scope of the invention, but rather as an exemplification of one preferred embodiment thereof Many other variation are possible. For example, the type of cells used or drug characteristics are unimportant to the method. The type of fluorescent cell labels used are also of little importance, as long as they can be readily detected by a fluorescence plate reader, and as long as the radiation opaque membrane of the migration plate is opaque to either the excitation or emission wavelengths of the fluorophore. The specific design or manufacture of the migration plate is unimportant as long as two suitable test chambers are separated by a radiation opaque membrane with pore sizes appropriate for the migration of the cell type being tested (typically 4–10 $\mu$m).

We claim:

1. A method for predicting the efficacy of anti-cancer drugs on cells wherein both the cytotoxic and anti-migratory effects of the drug are measured, comprising the steps of:

a. disaggregating a biopsy specimen into individual cells to form a cell suspension;

b. exposing said cells in said suspension to said anti-cancer drug;

c. adding said exposed cells to the first chamber of a migration plate comprising two chambers separated by a porous membrane, said porous membrane being opaque to radiation;

d. placing a chemical agent in the second chamber, said agent being capable of inducing migration of said cells from said first chamber to said second chamber;

e. incubating cells to allow cell migration to occur;

f. labeling cells on the side of the membrane closest to said second chamber with a fluorescent dye, said dye being capable of labeling only live cells;

g. labeling cells on the side of the membrane closest to said first chamber with a fluorescent dye, said dye being capable of labeling only dead cells;

h. stimulating the labeled cells on the side of the membrane closest to said second chamber with electromagnetic radiation of a first wavelength whereby said labeled cells will emit electromagnetic radiation of a second wavelength;

i. measuring the emitted electromagnetic radiation from the side of the radiation opaque membrane closest to said second chamber;

j. stimulating the labeled cells on the side of the membrane closest to said first chamber with electromagnetic radiation of a first wavelength whereby said labeled cells will emit electromagnetic radiation of a second wavelength; and k. measuring the emitted electromagnetic radiation from the side of the radiation opaque membrane closest to said first chamber, whereby the effect of a drug on said cell migration and said cell death is an indication of the effectiveness of said drug at arresting said cancer tissues.

2. The method according to claim 1, wherein:

said side of the membrane closest to the second chamber is coated with a fixed material capable of inducing migration.

3. The method according to claim 1, wherein:

said fluorescent dye capable of labeling only live cells is metabolically activated.

4. The method according to claim 1, wherein:

said fluorescent dye capable of labeling only live cells is embedded in a material endocytosed only by live cells.

5. The method according to claim 1, wherein:

the steps of stimulating the labeled cells on the side of the membrane closest to said first and said second chamber each further comprises the further step of measuring the electromagnetic radiation with a fluorescent plate reader.

6. A method for testing the efficacy of a drug on cells, in vitro, comprising the steps of:

exposing said cells in said suspension to said drug;

adding said exposed cells to the first chamber of a migration plate comprising two chambers separated by a porous membrane, said porous membrane being opaque to radiation;

placing a chemical agent in the second chamber, said agent being capable of inducing migration of said cells from said first chamber to said second chamber;

labeling cells on the side of the membrane closest to said second chamber with a fluorescent dye, said dye being capable of labeling only live cells;

labeling cells on the side of the membrane closest to said first chamber with a fluorescent dye, said dye being capable of labeling only dead cells;

stimulating the labeled cells on the side of the membrane closest to said second chamber with electromagnetic radiation of a first wavelength whereby said labeled cells will emit electromagnetic radiation of a second wavelength;

measuring the emitted electromagnetic radiation from the side of the radiation opaque membrane closest to said second chamber;

stimulating the labeled cells on the side of the membrane closest to said first chamber with electromagnetic radiation of a first wavelength whereby said labeled cells will emit electromagnetic radiation of a second wavelength; and measuring the emitted electromagnetic radiation from the side of the radiation opaque membrane closest to said first chamber, whereby the effect of said drug on said cell migration and said cell death is an indication of the effectiveness of said drug.

7. The method according to claim 6, wherein:

the steps of stimulating the labeled cells on the side of the membrane closest to said first and said second chamber each further comprises the further step of measuring the electromagnetic radiation with a fluorescent plate reader.

8. The method according to claim 6, wherein:

said fluorescent dye capable of labeling only live cells is metabolically activated.

9. The method according to claim 6, wherein:

said fluorescent dye capable of labeling only live cells is embedded in a material endocytosed only by live cells.

* * * * *

UNITED STATES PATENT AND TRADEMARK OFFICE
CERTIFICATE OF CORRECTION

PATENT NO.    : 6,448,030 B1
DATED         : September 10, 2002
INVENTOR(S)   : William L. Rust et al.

It is certified that error appears in the above-identified patent and that said Letters Patent is hereby corrected as shown below:

<u>Column 7,</u>
Line 60, change "a" to -- said --

Signed and Sealed this

Twenty-fourth Day of December, 2002

JAMES E. ROGAN
*Director of the United States Patent and Trademark Office*